US012721996B2

(12) United States Patent
Mech et al.

(10) Patent No.: US 12,721,996 B2
(45) Date of Patent: Sep. 1, 2026

(54) VIBRATORY NEUROMODULATION

(71) Applicant: The Alfred E. Mann Foundation for Scientific Research, Valencia, CA (US)

(72) Inventors: Brian Mech, Buffalo, MN (US); Robert Greenberg, Los Angeles, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 477 days.

(21) Appl. No.: 17/736,726

(22) Filed: May 4, 2022

(65) Prior Publication Data

US 2022/0355097 A1 Nov. 10, 2022

Related U.S. Application Data

(60) Provisional application No. 63/184,006, filed on May 4, 2021.

(51) Int. Cl.
*A61N 1/00* (2006.01)
*A61N 1/04* (2006.01)
(Continued)

(52) U.S. Cl.
CPC ......... *A61N 1/0456* (2013.01); *A61N 1/0476* (2013.01); *A61N 1/0484* (2013.01);
(Continued)

(58) Field of Classification Search
CPC .. A61N 1/0456; A61N 1/0476; A61N 1/0484; A61N 1/0492; A61N 1/0504; A61N 1/36021; A61N 1/36025; A61N 1/36031; A61N 1/36034; A61H 2201/5097; A61H 23/02; A61H 2201/1604; A61H 23/0245; A61H 23/0236; A61H 2201/165;
(Continued)

(56) References Cited

U.S. PATENT DOCUMENTS 6,436,029 B1 * 8/2002 Benderev .............. A61H 19/34
128/885
2004/0173220 A1 9/2004 Harry et al.
(Continued)

FOREIGN PATENT DOCUMENTS

WO 2019152136 A1 8/2019

OTHER PUBLICATIONS

International Search Report and Written Opinion issued for Int'l Appl. No. PCT/US22/72111, Int'l Filing Date May 4, 2022, mailed Jul. 7, 2022.

(Continued)

*Primary Examiner* — Benjamin J Klein
(74) *Attorney, Agent, or Firm* — ARENTFOX SCHIFF LLP

(57) ABSTRACT

The disclosure provides systems and methods for neuromodulation using a housing that at least partially contains a stimulator assembly, wherein the stimulator assembly is configured to generate vibration by mechanical oscillation and/or using a sound wave; and wherein the vibration generated by the stimulator assembly is configured to therapeutically treat the subject by stimulating one or more nerves when the housing is placed in proximity to or on a skin surface of a subject.

22 Claims, 6 Drawing Sheets

(51) Int. Cl.
*A61N 1/05* (2006.01)
*A61N 1/36* (2006.01)

(52) U.S. Cl.
CPC ......... *A61N 1/0492* (2013.01); *A61N 1/0504* (2013.01); *A61N 1/36021* (2013.01); *A61N 1/36025* (2013.01); *A61N 1/36031* (2017.08); *A61N 1/36034* (2017.08)

(58) Field of Classification Search
CPC .... A61H 2201/5005; A61H 2201/5012; A61H 2201/5035; A61H 2205/02; G16H 20/30; G16H 20/40; G16H 40/63; G16H 20/70; G16H 40/67; G16H 50/20; A61M 2021/0027; A61M 2021/0038; A61M 2021/0044; A61M 2021/0055; A61M 2205/0294; A61M 2205/332; A61M 2205/3553; A61M 2205/3592; A61M 2205/505; A61M 2205/52; A61M 2209/088; A61M 2210/06; A61M 2210/0662; A61M 2210/0687; A61M 2210/083; A61M 2230/04; A61M 2230/06; A61M 2230/10; A61M 2230/40; A61M 2230/60; A61M 2230/65; A61M 21/02; A61M 2021/0022; A61M 2205/8206; A61M 2230/205; A61M 2230/30
See application file for complete search history.

(56) References Cited

U.S. PATENT DOCUMENTS

| | | | | |
|---|---|---|---|---|
| 2007/0282400 | A1* | 12/2007 | Gorham | A61N 5/0616 607/151 |
| 2008/0319513 | A1* | 12/2008 | Pu | A61N 1/36139 607/62 |
| 2010/0249677 | A1* | 9/2010 | DiUbaldi | A61H 23/0245 601/46 |
| 2011/0166621 | A1 | 7/2011 | Cowan et al. | |
| 2012/0041333 | A1* | 2/2012 | Shelley | A61H 23/02 600/552 |
| 2015/0018728 | A1* | 1/2015 | Gross | A61N 1/375 607/116 |
| 2016/0303402 | A1 | 10/2016 | Tyler | |
| 2017/0165101 | A1* | 6/2017 | Davidian | A61H 23/02 |
| 2017/0165485 | A1* | 6/2017 | Sullivan | A61B 5/0022 |
| 2017/0326024 | A1* | 11/2017 | Hernandez | A61B 5/442 |
| 2018/0236202 | A1 | 8/2018 | Weiss et al. | |
| 2019/0001129 | A1* | 1/2019 | Rosenbluth | A61N 1/08 |
| 2019/0262223 | A1 | 8/2019 | Mitchell, Jr. | |
| 2020/0155840 | A1* | 5/2020 | Giannoukos | A61N 1/36031 |
| 2020/0390997 | A1 | 12/2020 | Jovanov | |

OTHER PUBLICATIONS

Extended European Search Report and Search Opinion received for European Application No. 22799798.8, mailed on Apr. 17, 2025, 12 pages.

* cited by examiner

VIBRATORY NEUROMODULATION

CROSS-REFERENCE TO RELATED APPLICATION

This application claims the benefit of U.S. Provisional Application Ser. No. 63/184,006, entitled "VIBRATORY NEUROMODULATION," which was filed on May 4, 2021, and is expressly incorporated by reference herein in its entirety.

BACKGROUND

Non-invasive neuromodulation techniques, including electrical stimulation have been demonstrated to be useful for a variety of conditions. For example, efforts have been made to treat pain and migraines using electrical stimulation. The effectiveness of non-invasive electrical stimulation is often constrained by the need to precisely target individual nerves for treatment, and due to working distance (depth) limitations, which limit treatment to accessible nerves close to the skin surface of the subject being treated. Moreover, at therapeutic levels, current devices can create sensations, skin irritation, and other side effects that are not pleasant. Transcranial stimulation such as magnetic (TMS) or Electroconvulsive Therapy (ECT) or direct current stimulation (DCS) have a larger working depth and stimulate larger areas in the brain, but they are typically administered through expensive pieces of capital equipment that must be accessed in a clinical environment, as opposed to being used at home. Accordingly, current devices, systems, and methods for minimal or non-invasive neuromodulation suffer from many drawbacks which limit widespread use of this technique as a therapeutic treatment. The present disclosure addresses these and other shortcomings in the art.

BRIEF SUMMARY OF EXEMPLARY ASPECTS OF THE DISCLOSURE

The devices, systems, and methods for minimal or non-invasive neuromodulation described herein address various shortcomings in the art, e.g., by relying upon the use of mechanical (e.g., vibratory) stimulation as a modality. Vibratory stimulation may be used to stimulate both the sympathetic and parasympathetic nervous systems. Furthermore, vibratory devices offer multiple benefits as compared to current electrical stimulation devices, including, e.g., such devices allow for a greater working depth compared to electrical stimulation, as well as a greater treatment area since vibrations are attenuated less quickly than an electrical field. The increased treatment area is also advantageous in that it requires less precise targeting by a user, as compared to electrical stimulation. Other advantages shall be described in further detail herein in the context of exemplary aspects or are otherwise apparent in view of the present disclosure.

In a first general aspect, the disclosure provides a neuromodulation device, comprising: a housing that at least partially contains a stimulator assembly, wherein the stimulator assembly is configured to generate vibration by mechanical oscillation and/or using a sound wave; and wherein the vibration generated by the stimulator assembly is configured to therapeutically treat the subject by stimulating one or more nerves when the housing is placed in proximity to or on a skin surface of a subject. In this exemplary aspect, the device comprises a singular stimulator assembly. However, it is expressly understood that any of the devices, systems, or methods described herein may include a plurality of stimulator assemblies, e.g., as illustrated by FIG. 1. Thus, any reference to an embodiment having a stimulator assembly should be recognized as also contemplating alternative embodiments comprising a plurality of stimulator assemblies. Each stimulator assembly may be independently controlled or otherwise configured to generate vibration at a different anatomical location and/or using different parameters.

In some aspects, the housing is adapted to be worn by, wrapped around at least a portion of, affixed to, placed on (or in proximity to) the skin surface of, the subject being treated. In some aspects, a housing containing the stimulator assembly may be placed directly on the skin surface of the subject or within 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 cm of the surface of the skin of the subject to be treated, or within a range bounded by any of the foregoing values. For example, the housing containing the stimulator assembly may be injected or implanted within 3 cm of the surface of the skin of the subject. In other aspects, the housing may be held against (or in proximity to) the skin surface of the subject by a patch or wrap to keep the housing within 3 cm of the skin surface while it is in use. In some aspects, the depth or distance of the housing may be measured from the point of the housing closest to the surface of the skin of the subject.

In some aspects, the stimulator assembly is configured to: a) generate vibration primarily in one direction; b) generate vibration in a plurality of directions, optionally using a member that translates a unidirectional vibration into vibration along one or more additional directions; and/or c) generate vibration at a constant or variable amplitude.

In some aspects, the stimulator assembly comprises a motor or piezoelectric element configured to cause the generation of the vibration by mechanical oscillation. It is understood that any mechanical and/or electronic source of vibration known in the art may be used in the devices, systems, and methods described herein.

In some aspects, the device further comprises a programmable memory containing settings for one or more parameters of the stimulator assembly (e.g., a frequency, amplitude, duration, and/or duty cycle of the vibration generated by the stimulator assembly).

In some aspects, the stimulator assembly is configured to generate vibration: a) at a frequency of about, at least, or exactly 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 20, 30, 40, 50, 60, 70, 80, 90, 100, 110, 120, 130, 140, 150, 160, 170, 180, 190, or 200 Hz, or at a frequency within a range bounded by any pair of the foregoing values; orb) at a frequency of about, at least, or exactly 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 Hz, or at a frequency within a range bounded by any pair of the foregoing values.

In some aspects, the housing may be adapted to be worn on, affixed to, or wrapped around a head of the subject. It is understood that in other aspects the housing may be adapted to be worn on, affixed to, wrapped around, or placed on any anatomical part of a human subject (or in proximity thereto). For example, in some aspects the housing is configured as a patch capable of being affixed to a skin surface of the subject using an adhesive (e.g., using glue or tape) or hook and loop fasteners. In still further aspects, the housing is implanted under the skin surface of the subject.

In a second general aspect, the disclosure provides a system for neuromodulation comprising any neuromodulation device as described herein, and a controller configured to adjust one or more parameters of the stimulator assembly. The one or more parameters may comprise, e.g., a frequency, amplitude, duration, and/or duty cycle of the vibration generated by the stimulator assembly. In some aspects, the controller is contained in a second housing separate from the housing containing the simulator assembly, and communicatively-linked to the stimulator assembly by a wired or wireless connection. In some aspects, the system is configured to allow a user to modify a frequency, amplitude, duration, and/or duty cycle of the vibration generated by the stimulator assembly, using software executed on a computer, smart phone, tablet, or dedicated controller. For example, the software may be configured to select one or more parameters for the vibration based on user input regarding a desired outcome of the treatment. In some aspects, the system further comprises one or more sensors configured to detect at least one physiological parameter. The system may, e.g., be configured to modulate one or more parameters of the vibration based on at least one physiological parameter detected by the one or more sensors.

In a third general aspects, the disclosure provides methods of treating a subject using any of the neuromodulation devices or systems (or components thereof) described herein. For example, in some aspects a method of treatment may comprise: a) providing a housing that at least partially contains a stimulator assembly, wherein the stimulator assembly is configured to generate vibration by mechanical oscillation and/or using a sound wave; b) placing the housing in proximity to or on a skin surface of the subject; c) stimulating one or more nerves of the subject by initiating vibration of the stimulator assembly; and d) reducing or eliminating one or more symptoms of a medical condition or disease, or improving the health of the subject.

In some aspects, the medical condition or disease comprises one or more of: a) chronic pain, acute pain, sciatica, fasciitis, myalgia, fibromyalgia, pain from an acute wound, a migraine, a headache, a cluster headache, orbital pain, ear pain, fatigued muscle pain, inflammatory pain, back pain, nerve pain, pain caused by cancer or a cancer treatment; or b) depression, epilepsy, movement disorders, chronic inflammation, rheumatoid arthritis, sleep disordered breathing, tinnitus, mood disorders, stress, anxiety, dementia, Alzheimer's Disease, Crohn's Disease, Irritable bowel syndrome, sepsis, lung injury, diabetes, traumatic brain injury, viral infections (e.g., a COVID-19 infection), Prader-Willy Syndrome, schizophrenia, hypertension, heart failure, cognitive impairment, a neuralgia, substance withdrawal, substance addiction, post-traumatic stress disorder (PTSD), over-active bladder, a pelvic floor disorder, or incontinence.

In some aspects, improving the health of the subject comprises an improvement to sleep quality and/or duration, or cognitive performance, of the subject.

In the methods of treatment contemplated herein, the neuromodulation device or system may include any of the components described herein. For example, the housing containing the stimulator assembly may be configured as an implant injected or surgically placed below the skin surface of the subject. Such methods may use a general-purpose device that can be programmatically configured to treat multiple medical conditions or diseases, or a specific-purpose device with settings (e.g., the frequency, amplitude, duration, and/or duty cycle of the vibration) programmed for the treatment of a specific medical condition or diseases. In some aspects, e.g., methods of treatment may comprise the use of neuromodulation systems, as described herein, wherein a user is allowed to select a desired outcome (e.g., improved sleep quality), and the system is configured to automatically select or modulate one or more settings of the treatment (e.g., any of the vibrations parameters described herein) to achieve the desired outcome, e.g., using a dedicated controller. In some aspects, such methods may comprise the use of a system designed to improve health or wellness (e.g., sleep duration or quality) in a subject unrelated to any specific medical condition or disease.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

DETAILED DESCRIPTION

Figure 1:
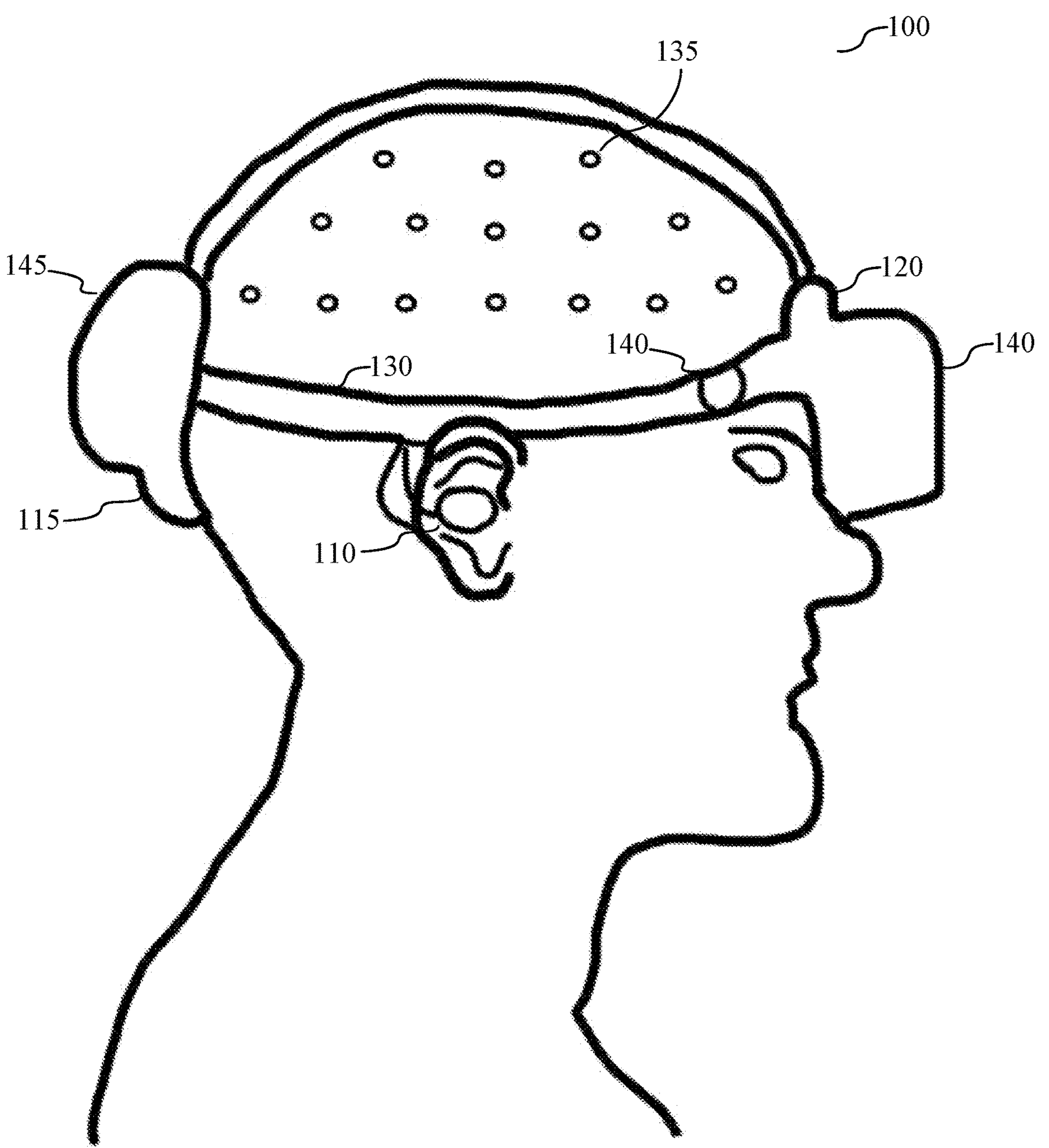
FIG. 1 is a diagram illustrating an exemplary embodiment of a vibration-based neuromodulation device in accordance with the present disclosure. This example illustrates a head-worn system that includes a plurality of stimulator assemblies.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of exemplary embodiments according to the present disclosure will now be presented with reference to various systems and methods. These systems and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented as a "processing system" or "controller" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), application-specific integrated circuits (ASICs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more exemplary embodiments, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

Non-invasive, minimally invasive, and invasive examples of neuromodulation have been developed over the last several decades in order to treat human illness. For example, prior research has studied stimulation of the vagus nerve, deep brain, occipital nerve, trigeminal nerve, tibial nerve, hypoglossal nerve, sacral nerve, phrenic nerve, sphenopalatine ganglion, and supraorbital nerve, as well as magnetic and direct current stimulation of the cortex and other brain structures. This research has led to the development of non-invasive devices for the treatment of a range of medical conditions and diseases, e.g., pain, migraines, inflammatory diseases such as irritable bowel and rheumatoid arthritis, movement disorders, tinnitus, depression, sleep-disordered breathing, post-traumatic stress disorder (PTSD), substance withdrawal, and others. Most non-invasive neuromodulation systems in use today rely upon electrical stimulation of a chosen target (e.g., one or more nerves or muscles). These devices have the advantage of being relatively inexpensive to produce and being relatively easy to use by a layperson. However, electrical stimulation has significant limitations, such as a low working distance (e.g., depth), requiring nerves to come close to the surface of the skin to be accessible, and it can be difficult to ensure that the intended target is actually being stimulated since there are anatomical differences between people and commercial devices often do not include a targeting system. Moreover, at therapeutic levels, these devices can create sensations, skin irritation, and other side effects that are unpleasant. Transcranial stimulation such as magnetic (TMS) or Electroconvulsive Therapy (ECT) or direct current stimulation (DCS) have a larger working depth and stimulate larger areas in the brain, but these techniques are typically administered through expensive pieces of specialized equipment that are only available in a clinical environment, rendering such methods unsuitable for home use and thus limiting their application. Ultrasonic stimulation has emerged as an alternative neuromodulation therapy, but this modality is also generally limited to a clinical environment and often requires sophisticated targeting.

In view of these and other shortcomings, there exists a need in the art for new devices, systems, and methods for neuromodulation. To that end, the present disclosure provides a solution that utilizes mechanical stimulation (e.g., vibratory stimulation). Prior to the present disclosure, relatively little research has been conducted regarding this modality. For example, penile vibratory stimulation has been used to treat erectile disfunction and other male sexual conditions, and there is some basic research showing that vibro-tactile stimulation can stimulate both the sympathetic and parasympathetic nervous systems. However, little attention has been directed to the use of vibratory stimulation is devices, systems, and methods of treatment as presently contemplated.

Vibratory stimulation offers multiple advantages over other minimally or non-invasive neuromodulation techniques. As used herein, minimally-invasive neuromodulation devices may include percutaneous structures that extend into the body below the surface of the skin to transfer vibrational energy into the body, as well as small devices that can be injected into the body (or inserted by some other minimally invasive means including a small incision or a trans-vascular approach). A percutaneous device may share many of the same features of a non-invasive device. In contrast, an implanted device will typically include a vibration source as well as a power source, which could be a battery (primary cell or rechargeable), or a circuit to receive power from outside the body. In one embodiment a small injectable housing contains a stimulator assembly comprising a vibration source (e.g., a piezoelectric element or motor) and a power supply capable of receiving power from an external source, such that when the means for applying power externally is in place (e.g., an RF coil) the device is actuated and capable of delivering vibratory stimulation to surrounding tissue (e.g., nerves and/or muscles) until the means for external power is removed or deactivated (e.g., by dedicated controller configured to communicate with the power supply).

The following disclosure shall focus primarily on non-invasive devices and systems. However, it is understood that minimally and non-invasive devices, including implantable devices, are expressly contemplated by the present disclosure. Accordingly, any discussion of neuromodulation devices or systems provided herein should be understood as also describing embodiments wherein some or all of the components or the device or system are injected (or implanted) into a subject, or provided via a percutaneous device. For example, the stimulator assemblies described herein may be incorporated (in whole or in part) into a housing to be injected or implanted into a subject (e.g., in a small housing to be injected subdermally within proximity to the surface of the subject's skin).

As noted above, vibratory stimulation using the devices provided herein offers various advantages. Perhaps most notably, such devices allow for a greater working depth compared to electrical stimulation. Related to this point, such devices also allow for a greater treatment area since vibrations are attenuated less quickly than an electrical field. Consequently, vibratory devices require less precise targeting compared to electrical stimulation, rendering such devices easier for use by a layperson (e.g., allowing for widespread use outside of a clinical environment). The vibratory devices described herein are thus easy to use, relatively inexpensive compared to electrical, ultrasonic, and other modalities, and can be used in an at-home setting. Furthermore, vibratory devices may cause fewer side effects (e.g., skin irritation) as compared to the unpleasant side effects observed when other modalities such as electrical stimulation are applied at therapeutic levels. Vibratory devices also offer the potential for multi-nerve or multi-target stimulation when placed in a location where more than one nerve or receptor is available to be stimulated (e.g., the ear, face, head, arm, leg, or neck). When one or more targets are present for stimulation, stimulation parameters (e.g., amplitude, pulse width, and/or frequency of vibration) may be tuned to selectively stimulate one target more than another. Vibratory stimulation also offers additional treatment options unavailable with prior modalities, e.g., it can be used to stimulate a feeling of relaxation and to improve sleep onset, duration, and quality.

Accordingly, in a general sense the devices, systems, and methods described herein may be used to provide vibratory stimulation to one or more regions of the human body to treat a medical condition or disease. In some aspects, vibratory stimulation may be combined with another form of stimulation (e.g., electrical, magnetic, etc.) in the same general region of the body or in a different region to augment the treatment of a given medical condition or disease, or to concurrently treat another medical condition or disease (e.g., one that is comorbid, and more amenable to a different treatment modality). Accordingly, the non-invasive neuromodulation techniques described herein may be used to treat various medical conditions and diseases, including without limitation pain, inflammation, cardiac issues, hypertension and other hemodynamic disorders, movement disorders, tinnitus, and many others.

In some exemplary aspects, a neuromodulation system may comprise a housing that at least partially contains a stimulator assembly configured to generate vibration by mechanical oscillation and/or using a sound wave. The housing may be adhered to the body (e.g., as a patch affixed to the skin using an adhesive or with hook and loop fasteners), wrapped around a portion of the body, or otherwise kept in proximity to a region of the body. The stimulator assembly may comprise a member or element that can mechanically oscillate, or produce a sound wave, in order to generate a vibration with a constant or variable amplitude. In some aspects, the stimulator assembly may be configured to generate vibration occurring primarily in one direction. However, in other aspects such devices may generate vibration in two or three dimension (e.g., the member may move in one, two, or three dimensions, or an attachment to the member may be used to translate a vibration in one direction into one or more other directions). For example, a stimulator assembly may include a ball at the end of piston that moves in and out, the ball indenting the skin of the subject and spreading vibrations spherically in the body. In some aspects, the housing may fully contain the stimulator assembly; in others, at least a portion of the stimulator assembly may be located outside of the housing. For example, the stimulator assembly may include an element configured to extend out of the housing and to generate vibration by transmitting a sound wave towards the surface of the subject's skin.

In some aspects, the housing may further contain, in whole or in part, additional components used by the neuromodulation device. For example, the housing may contain a means of activating the member or element that can mechanically oscillate or produce a sound wave (e.g., a motor, a piezoelectric element, a magnetic oscillator, a solenoid, or any other mechanical or electronic component for producing vibration known in the art). In some aspects, the housing may contain a power supply for the activator or for the member or element to enable vibration, such as a battery, or a power cord plugged into a wall outlet or another source of power.

In some aspects, neuromodulation devices as described herein may include memory configured to store settings for one or more parameters (e.g., frequency, amplitude, duration, or duty cycle settings for vibration) to be applied during treatment. For example, the memory may store settings for the treatment of various medical conditions or diseases. In some aspects, a subject may be allowed to select and/or modify settings for one or more of the parameters, e.g., using a physical or electronic interface included as part of the neuromodulation device. For example, the housing may include an LCD or LED screen configured to display one or more parameters (e.g., frequency, amplitude, duration, or duty cycle settings for vibration) and to allow a user to increase or decrease the level of any of these parameters (e.g., allowing a user to increase the frequency of vibration applied). In some aspects, the interface may allow a user to select a medical device or disease, or a desired outcome (e.g., relaxation, improved sleep quality) and the device may be configured to select predetermined or optimized parameters associated with the selection.

In some aspects, the neuromodulation device may be controlled using a separate controller (e.g., software executed on a dedicated controller, phone, tablet, watch, computer or other electronic device). In such aspects, the neuromodulation device is considered part of a neuromodulation system. The controller may be configured to provide an interface, similar to the interface contemplated for embodiments which include an integrated interface (e.g., as part of the housing). For example, the controller may include an LCD or LED screen configured to display one or more parameters (e.g., frequency, amplitude, duration, or duty cycle settings for vibration) and to allow a user to increase or decrease the level of any of these parameters (e.g., allowing a user to increase the frequency of vibration applied). In some aspects, the interface of the controller may allow a user to select a medical device or disease, or a desired outcome (e.g., relaxation, improved sleep quality) and the device may be configured to select predetermined or optimized parameters associated with the selection. Optionally, the controller may allow a third party to modify treatment parameters or to make selected as described above (e.g., the controller may allow a doctor or other medical professional to log-in from a remote location and to adjust the settings of the neuromodulation device). In some aspects, boundaries (e.g., minimum and maximum values) may be programmed for each parameter based on the limitations of the neuromodulation device or system. In some aspects, the controller may be programmed to include default or recommended values expected to be therapeutically effective for one or more medical conditions, diseases, or desired outcomes.

For example, the controller (or memory incorporated into the neuromodulation device) may be programmed to suggest (or allow) therapeutically-effective vibrational frequencies within the range of 50 Hz to 150 Hz, and to suggest (or allow) much lower or higher vibrational frequencies if a user selected relaxation as a desired outcome. In some aspects, frequencies in the range of 1.5 kHz to 20 kHz may be suggested as a level effective to block transmission of signals through a nerve (i.e., "nerve blocking"). In some aspects, frequencies between 0.1 Hz and 45 Hz may be used as therapeutic and/or for improving relaxation, or for easing stress and anxiety. The interface for the neuromodulation device or system may allow a user to select from a menu of desired potential outcomes (e.g. pain relief, relaxation, cardiac improvement, inflammation, cognitive performance). When a selection is made, the device may be configured to apply a default protocol to provide a therapy for the selected medical condition, disease, or desired outcome, which may or may not permit manual adjustment by the user. However, if it does permit manual adjustment, the boundaries for each parameter may, e.g., be a function of the desired outcome.

In some aspects, the interface may allow a user to be able to select a desired blend of outcomes, for example 80% pain relief, and 20% cognitive focus. This may result in an appropriately weighted multi-modal stimulation with two sets of parameters ($Fr_p$, $Amp_p$, $PW_p$, $DC_p$) and ($Fr_f$, $Amp_f$, $PW_f$, $DC_f$) where the two stimulation sets are delivered interleaved in the appropriate weighting, or one set for a period of time, and the second (third, fourth, fifth, etc.) set thereafter for the appropriate period of time. It may also be that a blending of the parameter sets is appropriate such that stimulation occurs at one set of parameters that depends only on the blend of desired outcomes. A blend may be, e.g., a linear blend. For the example described above in this passage, a linear blend may be: $Fr=0.8Fr_p+0.2Fr_f$, $Amp=0.8\ AMP_p\ 0.2\ Amp_f$, etc. However, this example is non-limiting and it is understood that other mathematical combinations (e.g., non-linear combinations) may be more appropriate.

In some aspects, a neuromodulation system may include one or more sensors to monitor and record physiological parameters, e.g., heart rate, heart rate variability, blood pressure, blood oxygen levels, sweat, conductivity, inflammation (including inflammatory biomarkers such as TNF or one or more Interleukins), ECG, EMG, EEG, autonomic balance, cardiac output, arterial blood pressure, and/or vascular resistance. Such data may be detected and/or measured by one or more sensors incorporated into the neuromodulation device (e.g., as an additional component within the housing). In other aspects, the sensor may be incorporated into a separate device, such as a smart watch worn by the subject which may include a pulse oximeter, heart rate detector, etc. In still further aspects, the neuromodulation system may include a plurality of sensors. For example, at least one sensor may be included in the housing of the neuromodulation device or in a separate housing communicatively-lined with the neuromodulation device or a separate controller, and/or at least one sensor may be incorporated into a separate device worn by or in proximity to the user (e.g., as part of a smart watch, or phone).

Data collected using the one or more sensors may be used to control one or more parameters of the vibration (amplitude, frequency, duty cycle, etc.), or to trigger activation or deactivation of vibration. For example, the neuromodulation device may include a control module configured to execute an algorithm that modulated, activates, or deactivates vibration based on the sensor data (e.g., determining that vibration is required, or has achieved its objective, or has triggered an abnormal or unintended response). This control functionality may alternatively be executed by software running on a separate controller, as described above. In some aspects, the neuromodulation device or system may be configured to record: a) one or more parameters of the vibration (frequency, pulse width, amplitude, duty cycle, period, etc.); b) changes made to the therapy during a session or over time, either by a user, a third party, or an automatic control algorithm, and the basis for a such change(s); and/or c) signals sensed by the one or more sensors, and optionally conclusions reached based on sensor signals (for example blood pressure was reduced by 15 points).

The collected data may be stored locally (e.g., in memory incorporated into the neuromodulation device or a separate controller) or transmitted to a remote or cloud-based storage. In some aspects, the neuromodulation device or system may include an interface for displaying any or all of the information that is recorded in both real time, and or after a therapy session, including metrics that may be calculated or imputed from the therapeutic session. In some aspects, the neuromodulation device or system may include a wired or wireless communications system capable of allowing communication with a computer or mobile device (e.g., BlueTooth or Wi-Fi). In some aspects, the neuromodulation device or system may be configured to transfer and/or store data on the computer or mobile device, or to connect to the cloud via the computer or mobile device, e.g., to upload this data. The collected and/or uploaded data may be analyzed by another person, or by using machine learning or artificial intelligence. A means for providing remote adjustment and/or remote troubleshooting via the cloud to the therapeutic device may also be provided.

As noted above, the vibration-based methods described herein may be paired with other modalities. Accordingly, neuromodulation devices and systems according to the disclosure may optionally include one or more additional stimulus mode(s) which provided, e.g., visual stimulus, sound stimulus, ultrasonic stimulus, electrical stimulus, and/or magnetic stimulus.

It should be appreciated that each of the individual components described herein may be incorporated into the housing of the neuromodulation device, or housed in one or more other devices that are communicatively linked to the neuromodulation device, or housed in a separate controller device capable of controlling multiple devices (e.g., via a wired or wireless connection). The multiple devices may include, e.g., a mobile phone, tablet, computer, dedicated controller, or other electronic device. Similarly, any of the functions described herein may be performed by software or hardware components incorporated into any of the aforementioned devices (e.g., the housing of the neuromodulation device, a separate housing communicatively-linked to the housing of the neuromodulation device, or a separate controller device).

It should also be appreciated that there are several potential targets on the body where vibrational stimulation could be used to modulate an illness or condition, and that the physical design and means of attachment for the first device, or plurality of devices, in the system to the body may vary depending on the stimulation target. For example, if the target were a limb, finger, toe, etc., the first neuromodulation device may be include in a housing designed to wrap around the entirety to the body feature, and have the member or element providing vibration in intimate proximity of the intended stimulation target. One simple way to do this would be to provide a cuff that would contain the housing of the first device (or be the housing of the first device) and an adjustable diameter to enable the cuff to go around the body feature and subsequently be tightened to ensure proximity to the skin (for example a hook and loop based cuff as typically used for a sphygmomanometer). For embodiments where the exact pressure of the vibratory element against the skin may be important, a mechanical limiter may be used. Alternatively, in some aspects, one or more pressure sensors that provide feedback to the user or a mechanical control system that is adjusting the tightness of the cuff may be used.

While a cuff-based embodiment may be useful in many aspects, such configurations are not the only means of attaching the housing of the neuromodulation device, or any communicatively-linked devices (e.g., containing additional sensors), to the body. For example, in some aspects the neuromodulation device housing may be included within a patch or the housing itself may form the patch, as another viable means for attaching the first device to the body. This patch may be attached using an adhesive, including an adhesive that can be activated and deactivated by some means to attach and release the patch from the body. Other methods of attachment may take advantage of anatomical features that provide easy means of attachment. For example, if the nose or the sub-orbital or supra-orbital region, or the temporal region or the side of the head (or all of these) were a desired stimulation target, the neuromodulation device may be kept in proximity to the target(s) using a glasses-like structure, a goggles-like structure, or a halo-like structure such as that used in virtual or augmented reality. Where visual stimulation and or sound presentation is desired concurrent with vibrational stimulation, this may be a preferred structure. For example, a neuromodulation device may be incorporated into a hat or halo-like embodiment intended to be worn on the head, optionally with augmented or virtual reality functionality and/or speakers, to provide audio and/or visual stimulation in addition to vibration-based neuromodulation. An example of such a device is shown in FIG. 1.

FIG. 1 is a diagram illustrating an exemplary embodiment of a neuromodulation device 100 that includes a first stimulator assembly 110, a second stimulator assembly 115, and a third stimulator assembly 120, which are each at least partially contained in a housing 130 designed to be worn on the head of a subject. The first stimulator assembly 110, second stimulator assembly 115, and third stimulator assembly 120 may be independently controlled (e.g., each may be subject to different vibration parameters, and as shown by the figure these assemblies are directed to different anatomical targets). In this case, the first stimulator assembly 110 is an ear assembly that includes a speaker configured to transmit sound and a vibrational member to stimulate cranial nerves 5, 7, 9, 10, V3 (mandibular) and auricular nerves C2 and C3. The second stimulator assembly 115 is positioned at the rear of the subject's head and is configured to provide unilateral or bilateral stimulation of the occipital nerve. The third stimulator assembly 120 is positioned at the front of the subject's head and is configured to provide stimulation to the supra-orbital and/or trigeminal nerve.

In this case, the housing 130 is configured as a halo support which also includes a visual display (e.g., to provide visual stimulation during or in addition to vibration-based neuromodulation). The visual display 140 may be used, e.g., to provide cognitive behavioral therapy, training, relaxation, exposure therapy, psychotherapy, desensitization, entertainment, and/or distraction during the neuromodulation treatment. The halo support is shown to be connected to a scalp EEG system 135 and a temporal pulse sensor 140. Data from these sensors may be used by the neuromodulation device 100 to modulate one or more parameters of the stimulator assemblies as described above. The housing 130 includes a rechargeable battery 145 to power the neuromodulation system, memory configured to store collected sensor data and parameters for the neuromodulation (e.g., parameters for each stimulator assembly, and parameters for the audio/visual stimulation provided by the visual display 140), cables to transmit power and data between the components of the neuromodulation device 100. In some aspects, a neuromodulation device 100 may also include a wired or wireless communications system (e.g., integrated into the housing 130 or in a separate housing), to communicate with one or more sensors or external devices (e.g., using Bluetooth), as illustrated by the following exemplary embodiment.

Figure 2:
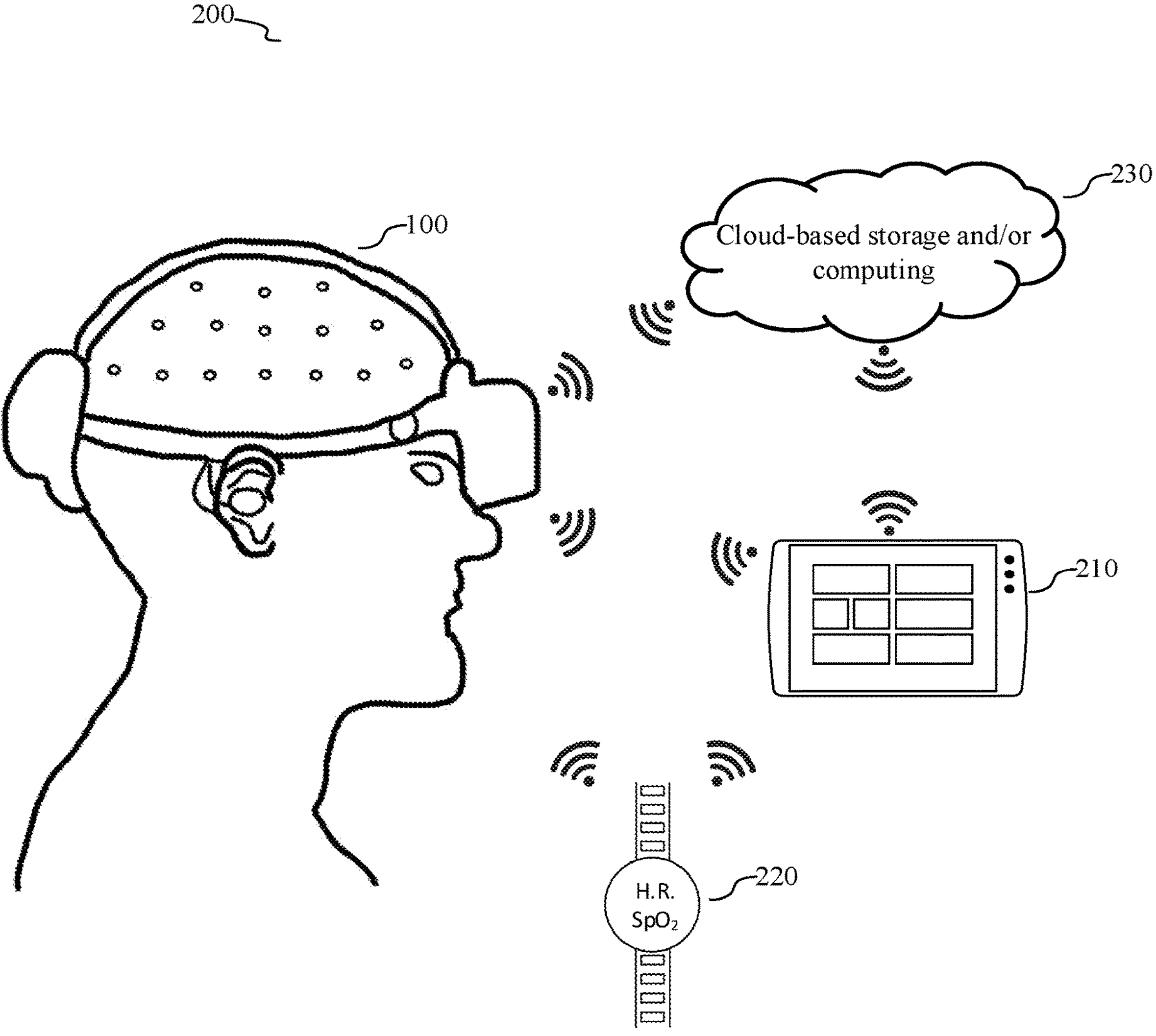
FIG. 2 is a diagram illustrating an exemplary embodiment of a vibration-based neuromodulation system in accordance with the present disclosure, which includes a dedicated controller configured to communicate with and modify parameters of the vibration generated by the stimulator assembly, as well as a paired smart watch that includes sensors configured to detect physiological parameters, providing additional data for the system to utilize.

FIG. 2 illustrates a neuromodulation system 200 that pairs the neuromodulation device 100 of FIG. 1 with a dedicated controller 210 and an external device 220 housing additional sensors (in this case, a smart watch). As explained above, a neuromodulation device 100 in accordance with the disclosure may be communicatively-linked with additional components. Here, the neuromodulation device 100 is shown to be wirelessly connected to a wrist-worn external device 220 in the form of a smart watch that includes a plurality of sensors configured to collect data regarding the subject's heart rate, blood pressure, SpO2, and blood flow. The neuromodulation device 100 and the external device 220 are both shown to be wirelessly connected with a dedicated controller 210, which is configured to allow a subject (or third party) to control one or more parameters of the neuromodulation device 100 (e.g., the frequency, duration, or amplitude of vibration generated by any of the three stimulator assemblies). The dedicated controller 210, in this example, is further configured to collect sensor data from the neuromodulation device 100 and from the sensors incorporated not the external device 220. The interface of the dedicated controller 210 displays a real-time summary of the sensor data and current parameters for the neuromodulation device 100. In some aspects, the dedicated controller 210 may be configured to transmit parameters or settings to the neuromodulation device 100, and/or to record and/or analyze sensor data collected by sensors incorporated into the neuromodulation device 100 or the external device 220. The dedicated controller 210 may further be configured to execute one or more algorithms to automatically select parameters or settings for the neuromodulation device 100, e.g., based on preset defaults, collected sensor data, and/or input from the subject or a third party. For example, the dedicated controller 210 may be configured to decrease or terminate vibrational stimulation if the sensor data shows a sudden and sharp increase in heart rate. The dedicated controller may allow a user to select treatment options (e.g., a medical condition or disease to be treated) or a desired outcome (e.g., relaxation) as described above, and may select treatment settings or parameters based on this input. In some aspects, the dedicated controller 210 and/or the neuromodulation device 100 may be configured to communicate with a cloud-based storage and/or computing resource 230. For example, data collected from one or more sensors integrated into the neuromodulation device 100, or the external device 220, may be uploaded to the cloud-based storage and/or computing resource 230 for storage or processing. For example, the neuromodulation system 200 may be configured to store periodic backups of collected sensor data in the cloud. Furthermore, the neuromodulation device 100 and/or the dedicated controller 210 may be configured to obtain parameters for the vibrational stimulation from the cloud-based storage and/or computing resource 230. For example, the neuromodulation device 100 and/or the dedicated controller 210 may be configured to receive input from the subject to be treated or a third party (e.g., a clinician) regarding a medical condition or disease to be treated, or a desired outcome (e.g., relaxation), and to obtain corresponding parameters for the vibrational stimulation from the cloud-based storage and/or computing resource 230.

Figure 3:
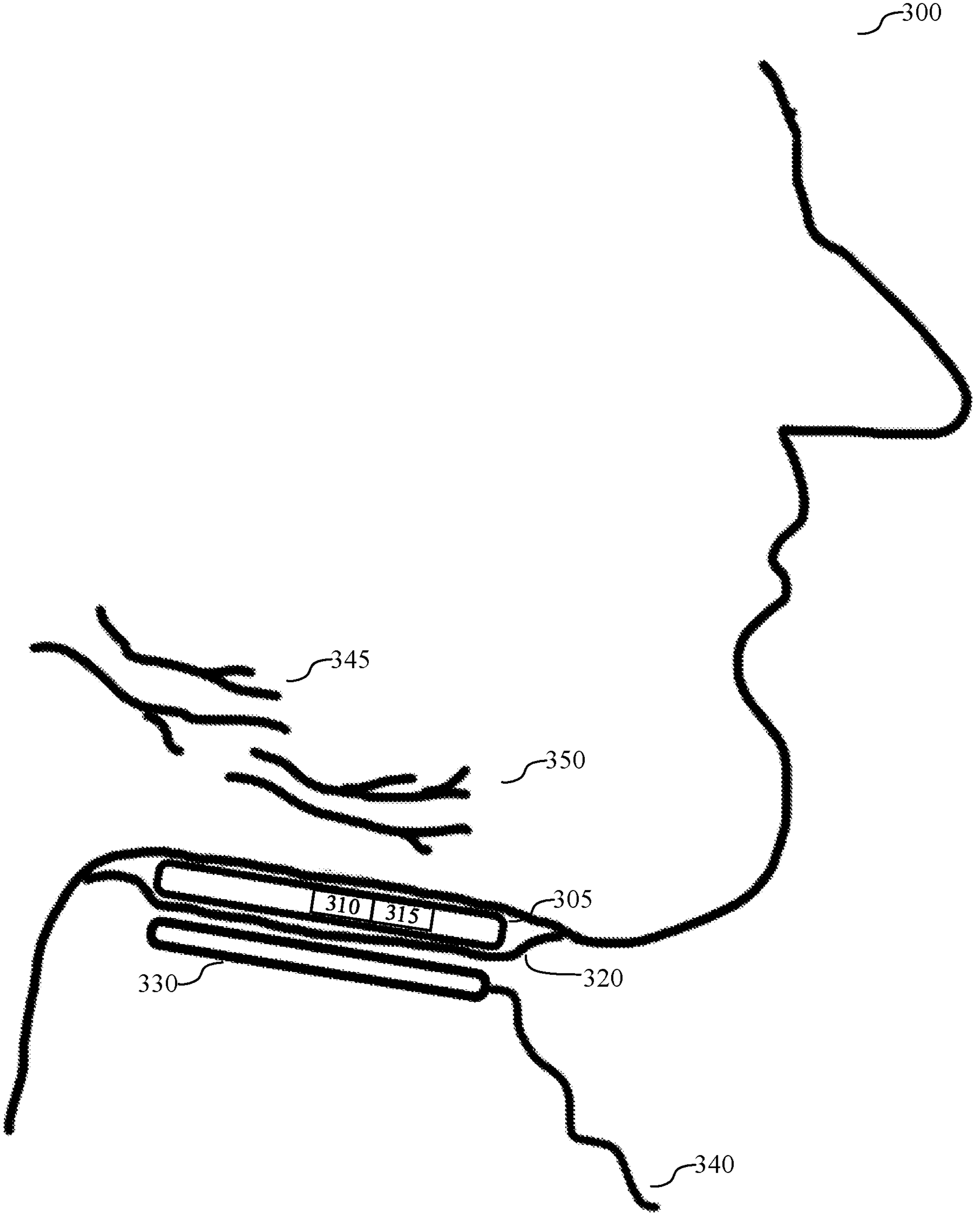
FIG. 3 is a diagram illustrating an exemplary embodiment of a non-invasive vibration-based neuromodulation system in accordance with the present disclosure. In this example, the stimulator assembly is contained in a housing configured to be affixed to the surface of the jaw of a subject (e.g., as an adhesive patch). As demonstrated by this example, neuromodulation systems as described herein may be configured to allow wireless charging of the power source for the stimulator assembly.
Figure 4:
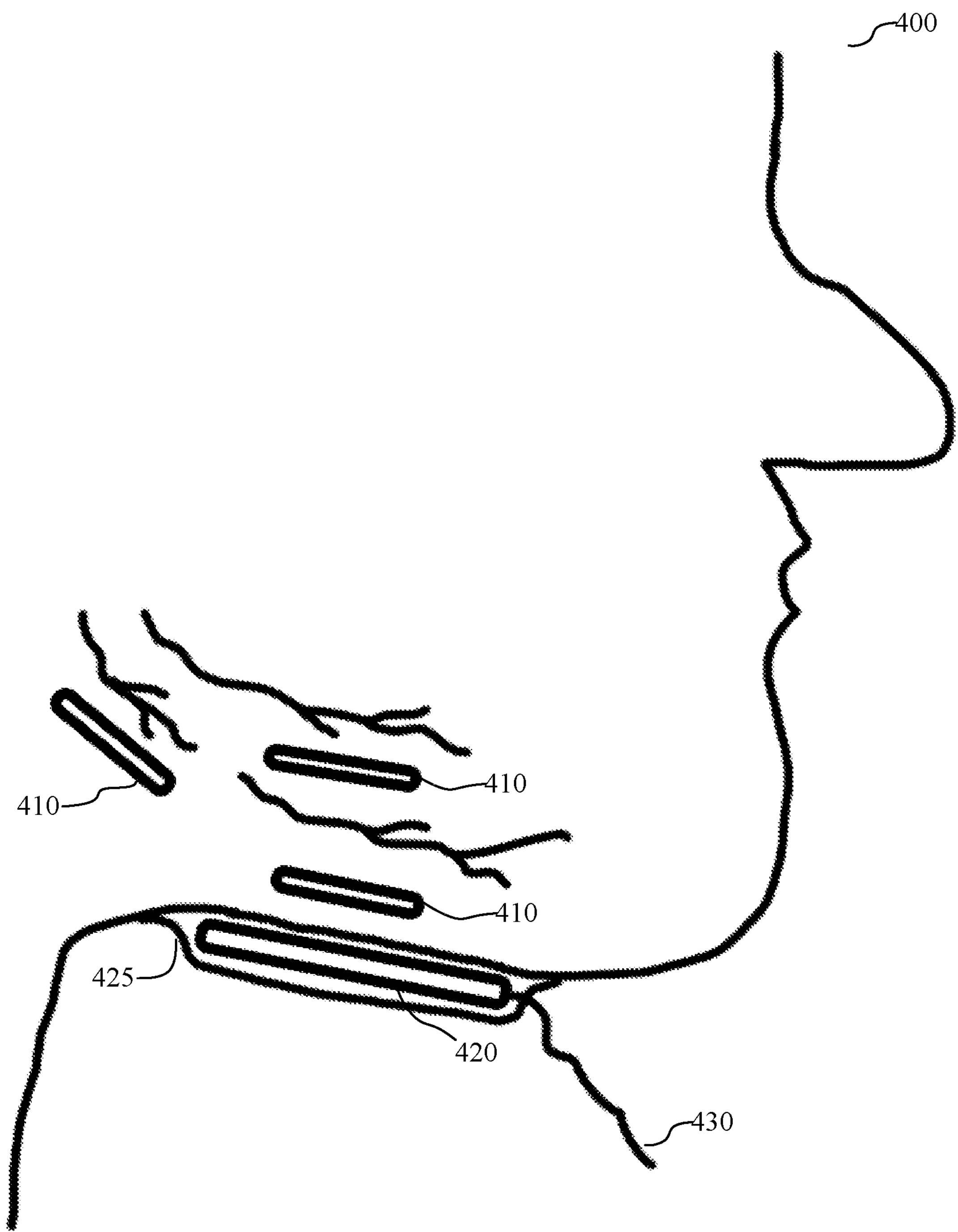
FIG. 4 is a diagram illustrating an exemplary embodiment of a minimally-invasive vibration-based neuromodulation system in accordance with the present disclosure. In this example, the stimulator assembly is contained in a housing implanted under the surface of the skin of the subject, in proximity to the jaw of a subject. This example illustrates the use of an external charging device capable of wireless charging the power source for the implanted stimulator assembly.

FIG. 3 and FIG. 4 show two potential vibratory neuromodulation systems to treat sleep apnea. Both the hypoglossal and glossopharyngeal nerves pass relatively close to the surface of the skin in the chin, making this an optimal location to stimulate these nerves using vibration to achieve and maintain airway patency. This can be done externally as shown in FIG. 3 with a vibratory device secured to skin under the chin and near the neck, or through a minimally-invasive implantable solution injected near one or both nerves (one implant between both, or one implant for each may be ideal configurations) as shown by FIG. 4. Note that a percutaneous solution is also contemplated, although not shown in these figures. In either case, a signal indicative of airway blockage or expected airway blockage (e.g., detected using a sensor included in the same housing as the stimulator assembly or in a separate housing) could be used to time the stimulation. Alternatively, a respiratory signal may also be used to time stimulation.

In particular, FIG. 3 shows a neuromodulation system 300 for treating sleep apnea comprising a housing 305 containing a stimulator assembly 310 and a control module 315 comprising memory and a processor configured to execute the control logic governing the operation of the stimulator assembly 310. The housing 305 is held in place on the surface of the subject's chin by an adhesive patch 320. In this example, the stimulator assembly 310 is powered wirelessly by a power supply contained in a second housing 330, which is in turn connected to power (e.g., a wall outlet) via a power cord 340. The stimulator assembly 310 is consequently powered and capable of providing vibratory stimulation when the second housing 330 is plugged in to a power source via the power cord 340 and placed in proximity to the housing 305. The control module 315 may be configured to execute one or more algorithms which control operation of the stimulator assembly 310 based on sensor data collected by one or more sensors incorporated into the housing 305, second housing 330, or a remote sensor (e.g., an accelerometer in a third housing 335 placed on the chest of the subject, which detects a respiration signal). For example, the control module 315 may be configured to trigger stimulation of the glossopharyngeal 345 and/or hypoglossal 350 nerves based on the sensor signal(s) in order to achieve airway patency.

In some alternative aspects, the stimulator assembly 310 may be configured to provide constant stimulation while the housing 305 is in position using predefined or programmable parameters, or to stimulate based on a timing signal (e.g., provided wirelessly or via a wire to either the housing 305 or the second housing 330). Furthermore, it is contemplated that in alternative aspects the housing 305 may include its own source of power (e.g., a rechargeable battery) that can last for the duration of a night. In such cases, the second housing 330 would be unnecessary, or provided as an optional secondary power source.

FIG. 4 illustrates a similar embodiment of a neuromodulation system 400 for treating sleep apnea using a stimulator assembly 405 contained in a housing 410 injected under the skin of the subject. In some cases, a single injected housing 410 may suffice to provide effective treatment. However, depending on the severity of the subject's sleep apnea and/or the specific pathology of the subject, additional stimulation may be desirable (e.g., to target multiple nerves). Accordingly, this figure shows three injected housings 410, each containing a stimulator assembly 405. Each injected housing 410 may contain a control module 415 comprising memory and a processor configured to execute the control logic governing the operation of the stimulator assembly 405.

In this example, each stimulator assembly 405 is powered wirelessly by a power supply contained in an external housing 420, which is affixed to the subject's chin as an adhesive patch 425 and in turn connected to power (e.g., a wall outlet) via a power cord 430. Each stimulator assembly 405 is consequently powered and capable of providing vibratory stimulation when the external housing 420 is plugged in to a power source via the power cord 430 and placed in proximity to the injected housings 410. Each control module 415 may be configured to execute one or more algorithms which control operation of the respective stimulator assembly 405 based on sensor data collected by one or more sensors incorporated into the injected housing 410, external housing 420, or a remote sensor (e.g., an accelerometer in a third housing 435 placed on the chest of the subject, which detects a respiration signal). For example, each control module 415 may be configured to trigger stimulation of the glossopharyngeal and/or hypoglossal nerves based on the sensor signal(s) in order to achieve airway patency. In this case, since multiple injected housings 410 are used, each containing a distinct control module 415 executing independent control logic, the vibrational stimulation may be customized for each nerve (e.g., the glossopharyngeal and hypoglossal nerves may be triggered independently), allowing for a delay, offset, etc. as may be desirable to treat sleep apnea in some subjects.

In some alternative aspects, each injected housing 410 may include its own power source (e.g., a rechargeable battery). In such cases, the external housing 420 may then function as a charger or as the source (or a secondary source) of the control logic used to control operation of each stimulator assembly 405. Alternatively, the control logic may be executed on another device (e.g., a dedicated controller or phone—not shown) that is in wireless communication with the injected housings 410.

Figure 5:
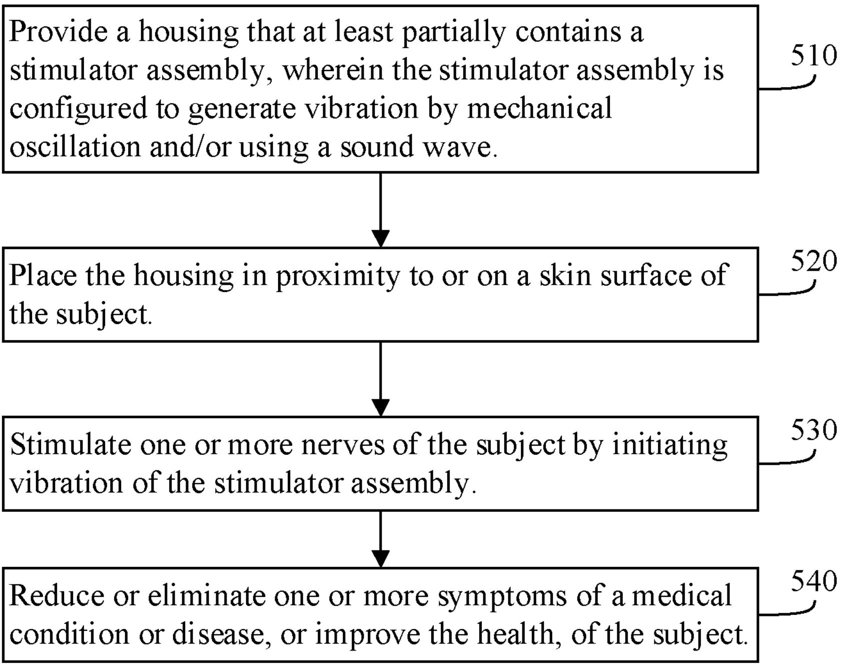
FIG. 5 is a conceptual flow diagram of a process for treating a medical condition or disease, or improving the health, of a subject, using a neuromodulation device according to an exemplary aspect of the disclosure.

FIG. 5 is a diagram illustrating an exemplary method for treating a subject using a neuromodulation device according to the disclosure. In this example, the method begins at step 510 by providing a housing that at least partially contains a stimulator assembly, wherein the stimulator assembly is configured to generate vibration by mechanical oscillation and/or using a sound wave. The housing is next placed in proximity to or on a skin surface of the subject, at step 520. At step 530, one or more nerves of the subject are then stimulated by initiating vibration of the stimulator assembly. As a result, at step 540 one or more symptoms of a medical condition or disease of the subject are reduced or eliminated, or the health of the subject is improved.

In some aspects, stimulation of one or more nerves of the subject may comprise the application of vibrational stimulation provided by a stimulator assembly configured to: a) generate vibration primarily in one direction; b) generate vibration in a plurality of directions, optionally using a member that translates a unidirectional vibration into vibration along one or more additional directions; and/or c) generate vibration at a constant or variable amplitude.

In some aspects, stimulation of one or more nerves of the subject may comprise the application of vibrational stimulation for at least, at most, about, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes, or for a length of time bounded by any of the foregoing values. In some aspects, the vibrational stimulation may be applied (e.g., for any duration described herein), followed by a rest or pause period wherein no stimulation is applied, and one or more rounds of additional vibrational stimulation (e.g., for any duration described herein). For example, a neuromodulation device or system according to the disclosure may be configured to apply stimulation for 5 minutes, pause for 2 minutes, and then apply stimulation for 10 minutes. It is understood that in some aspects, the stimulation may be applied a plurality of times (e.g., 1, 2, 3, 4, 5, 6, 7, 8, 9, or 10 times), with each application separated by a pause state wherein stimulation is not applied. The duration of each pause, and the stimulation parameters (e.g., duration, frequency, amplitude), may be independently selected for each pause state and for each application state.

In some aspects, a neuromodulation device or system according to the disclosure may be configured to apply vibrational stimulation using a first set of parameters (e.g., duration, frequency, and/or amplitude) and then to modulate the vibrational stimulation by adjusting one or more of the first set of parameters. For example, the frequency or amplitude of the vibrational stimulation may be gradually increased or decreased over 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes, or over a length of time bounded by any of the foregoing values. Gradual modulation may be useful in particular application, e.g., when a neuromodulation device is applying a treatment to improve relaxation or sleep quality.

In some aspects stimulation of one or more nerves of the subject may comprise the application of vibrational stimulation a) at a frequency of about, at least, or exactly 10, 20, 30, 40, 50, 60, 70, 80, 90, 100, 110, 120, 130, 140, 150, 160, 170, 180, 190, or 200 Hz, or at a frequency within a range bounded by any pair of the foregoing values; or b) at a frequency of about, at least, or exactly 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 Hz, or at a frequency within a range bounded by any pair of the foregoing values.

As indicated above, the neuromodulation devices described herein may be used to treat a variety of medical conditions and diseases, and to improve the health of a subject (e.g., by increasing sleep quality or duration, or reducing stress). This disclosure contemplates stimulation anywhere on the body, or in the body, where the vibratory stimulus can be provided in a minimally or non-invasive form as described above. Although not intended as an exhaustive set, the list of potential targets for neuromodulation including the devices and systems described herein includes: any nerve from the family of vagus, phrenic, sacral, tibial, hypoglossal, pharyngeal, glossopharyngeal, occipital, spinal, cranial, cavernous, facial, radial, ulnar, auditory, esophageal, laryngeal, femoral, frontal, cardiac, cervical, hypogastric, plantar, mandibular, perineal, pelvic, saphenous, splenic, tympanic, renal, thoracic, vestibular and trigeminal nerves, and any of their branches; the heart, carotid sinus, vocal cords, tongue, muscles; anatomical targets, including nearby nerves and muscles, such as the ear(s), forehead, nose, chin, cheek, back of the head, neck, shoulder, spine, arm(s), wrist(s), elbow(s), finger(s), stomach, chest, leg(s), penis, clitoris, anus, knee(s), foot, feet, and toe(s). For example, in some aspects the devices and systems described herein may be used to provide external vibratory stimulation of the tibial and/or saphenous nerve, either unilaterally or bilaterally on the foot, ankle, calf, or leg (including multiple and/or different locations on each leg), using a cuff, and/or adhesive, and/or suction to hold the stimulator in place. Stimulation of either the tibial nerve or saphenous nerve, or both, could be used to treat pelvic floor disorders including incontinence (fecal and/or urinary) and/or overactive bladder syndrome.

The neuromodulation devices and systems described herein also offers the potential to treat various human medical conditions and diseases, including those for which other stimulation techniques have been demonstrated to be effective. As a non-exhaustive set, this list includes: chronic pain, acute pain, sciatica, fasciitis, myalgia, fibromyalgia, acute wound, migraine, headaches, cluster headaches, orbital pain, ear pain, fatigued muscle pain, inflammatory pain, back pain, nerve pain, cancer pain (including pain from cancer treatment); conditions treated by neuromodulation including depression, epilepsy, movement disorders, chronic inflammation, rheumatoid arthritis, sleep-disordered breathing, tinnitus, mood disorders, stress, anxiety, dementia, Alzheimer's Disease, Crohn's Disease, Irritable bowel syndrome, sepsis, lung injury, diabetes, traumatic brain injury, viral infections (e.g., COVID-19 infections), Prader-Willy Syndrome, schizophrenia, hypertension, heart failure, cognitive impairment, neuralgias, substance withdrawal, substance addiction, PTSD, over-active bladder, pelvic floor disorders, and incontinence, among others. Moreover, the present devices and systems can be used as a treatment to improve to promote wellness, better sleep, better cognitive performance, and better learning in healthy subjects.

Figure 6:
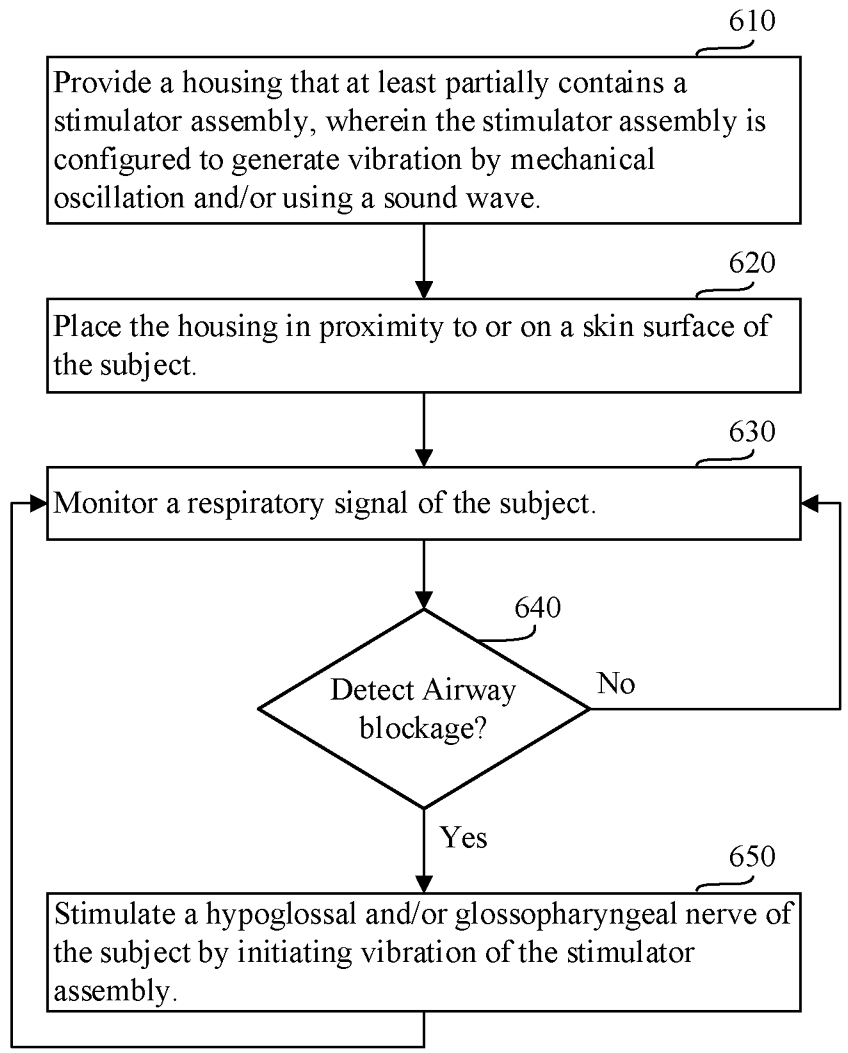
FIG. 6 is a conceptual flow diagram of a process for treating sleep apnea using a neuromodulation system according to an exemplary aspect of the disclosure.

FIG. 6 is a diagram illustrating another exemplary method for treating a subject using a neuromodulation system according to the disclosure. In this case, the method is directed to the treatment of sleep apnea and the neuromodulation system includes a neuromodulation device paired with a sensor configured to monitor a respiratory signal of the subject. The method begins at step 610 by providing a housing that at least partially contains a stimulator assembly, wherein the stimulator assembly is configured to generate vibration by mechanical oscillation and/or using a sound wave. Next, the housing is placed in proximity to or on a skin surface of the subject. In this case, the housing would typically be placed on the lower face of the subject's chin (i.e., in proximity to the hypoglossal and glossopharyngeal nerves). At 630, the system monitors a respiratory signal of the subject (e.g., sensed using an accelerometer in a separate housing placed on or in proximity to the subject's chest). If an airway blockage is detected based on the respiratory signal at step 640, the system would then trigger stimulation of a hypoglossal and/or glossopharyngeal nerve of the subject, at step 650, by initiating vibration of the stimulator assembly. If not, or following stimulation, the system would return to monitoring the respiratory signal at step 630. The aforementioned control logic may be executed using a processor and memory included in the same housing as the stimulator assembly. In other aspects, this control logic may be performed by a dedicated controller or other electronic device communicatively linked to the stimulator assembly, as described above.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases “consisting of” or “consisting essentially of” in lieu of or as an amended for “comprising.” When used in the claims, whether as filed or added per amendment, the closed-ended transitional phrase “consisting of” excludes any element, limitation, step, or feature not expressly recited in the claims. The closed-ended transitional phrase “consisting essentially of” limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase “comprising” is being defined as encompassing all the specifically recited elements, limitations, steps and/or features as well as any optional, additional unspecified ones. The meaning of the closed-ended transitional phrase “consisting of” is being defined as only including those elements, limitations, steps and/or features specifically recited in the claim whereas the meaning of the closed-ended transitional phrase “consisting essentially of” is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase “comprising” (and equivalent open-ended transitional phrases thereof) includes within its meaning, as a limiting case, claimed subject matter specified by the closed-ended transitional phrases “consisting of” or “consisting essentially of” As such embodiments described herein or so claimed with the phrase “comprising” are expressly or inherently unambiguously described, enabled and supported herein for the phrases “consisting essentially of” and “consisting of.”

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A method of treating a pelvic floor disorder in a subject in need thereof, comprising:

providing a neuromodulation system, comprising i) a housing that at least partially contains a stimulator assembly, wherein the stimulator assembly is configured to generate vibration by mechanical oscillation using a member that translates a unidirectional vibration into vibration along one or more additional directions and using a sound wave, and ii) a controller, wherein the controller is configured to adjust one or more parameters of the stimulator assembly;

placing the housing on a skin surface of the subject;

stimulating a tibial nerve and a saphenous nerve of the subject by initiating vibration of the stimulator assembly, wherein the vibration generated by the stimulator assembly is configured to stimulate the tibial nerve and/or the saphenous nerve of the subject when the housing is placed on the skin surface of the subject; and reducing or eliminating one or more symptoms of the pelvic floor disorder experienced by the subject, wherein the pelvic floor disorder comprises incontinence and/or overactive bladder syndrome.

2. The method of claim 1, wherein the housing is adapted to be worn by, wrapped around a portion of, or placed on, the skin surface of the subject being treated.

3. The method of claim 1, wherein the one or more parameters comprise a frequency, amplitude, duration, and/or duty cycle of the vibration generated by the stimulator assembly.

4. The method of claim 1, wherein the controller is contained in the housing or in a second housing, and communicatively-linked to the stimulator assembly by a wired or wireless connection.

5. The method of claim 1, wherein the stimulator assembly is further configured to:

a) generate vibration primarily in one direction; and/or b) generate vibration at a constant or variable amplitude.

6. The method of claim 1, wherein the stimulator assembly comprises a motor, a piezoelectric element, a magnetic oscillator, or a solenoid, configured to cause the generation of the vibration by mechanical or soundwave oscillation.

7. The method of claim 1, further comprising a programmable memory that contains settings for one or more parameters of the stimulator assembly, wherein the one or more parameters comprise a frequency, amplitude, duration, and/or duty cycle of the vibration generated by the stimulator assembly.

8. The method of claim 1, wherein the stimulator assembly is configured to generate vibration:

a) at a frequency of 10, 20, 30, 40, 50, 60, 70, 80, 90, 100, 110, 120, 130, 140, 150, 160, 170, 180, 190, or 200 Hz, or at a frequency within a range bounded by any pair of the foregoing values; or b) at a frequency of 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 Hz, or at a frequency within a range bounded by any pair of the foregoing values.

9. The method of claim 1, wherein the neuromodulation system is configured to allow a user to modify a frequency, amplitude, duration, and/or duty cycle of the vibration generated by the stimulator assembly, using software executed on a computer, smart phone, tablet, or dedicated controller.

10. The method of claim 9, wherein the software is configured to select one or more parameters for the vibration based on user input regarding a desired outcome of the treatment.

11. The method of claim 1, wherein the controller is configured to cause the stimulator assembly to generate a vibration having a frequency of 1.5 kHz to 20 kHz.

12. The method of claim 1, wherein the neuromodulation system is further configured to provide one or more additional stimuli to the subject selected from visual, sound, ultrasonic, electrical, and/or magnetic stimulation; and the controller is further configured to adjust one or more parameters of the one or more additional stimuli.

13. The method of claim 12, wherein the neuromodulation system is further configured to provide visual stimulation to the subject; and the controller is further configured to adjust one or more parameters of the visual stimulation.

14. The method of claim 12, wherein the neuromodulation system is further configured to provide magnetic stimulation to the subject; and the controller is further configured to adjust one or more parameters of the magnetic stimulation.

15. The method of claim 1, wherein the vibration generated by the stimulator assembly is configured to stimulate the tibial nerve and the saphenous nerve of the subject when the housing is placed on the skin surface of the subject, thereby treating the pelvic floor disorder experienced by the subject.

16. The method of claim 1, wherein the stimulator assembly is configured to generate vibration primarily in one direction.

17. The method of claim 1, wherein the stimulator assembly is configured to generate vibration in a plurality of directions, using a member that translates a unidirectional vibration into vibration along one or more additional directions.

18. The method of claim 1, wherein the stimulator assembly is configured to generate vibration at a constant or variable amplitude.

19. A method of treating sleep apnea in a subject in need thereof, comprising:

providing a neuromodulation system comprising i) a housing that at least partially contains a stimulator assembly, wherein the stimulator assembly is configured to generate vibration by mechanical oscillation using a member that translates a unidirectional vibration into vibration along one or more additional directions and using a sound wave, ii) a controller, wherein the controller is configured to adjust one or more parameters of the stimulator assembly;

and iii) one or more sensors;

placing the housing on a skin surface of a chin or a neck of the subject;

stimulating a hypoglossal and/or a glossopharyngeal nerve of the subject by initiating vibration of the stimulator assembly;

adjusting, by the controller, a frequency, amplitude, duration, and/or duty cycle of the vibration generated by the stimulator assembly based on a respiration signal for the subject determined based upon data collected from the one or more sensors; and reducing or eliminating one or more symptoms of the sleep apnea experienced by the subject.

20. The method of claim 19, wherein the one or more symptoms of the sleep apnea comprises: sleep disordered breathing.

21. The method of claim 19, wherein stimulating the hypoglossal and/or the glossopharyngeal nerve of the subject causes an improvement to sleep quality and/or duration, or cognitive performance, of the subject.

22. The method of claim 19, wherein the stimulating step comprises stimulating both the hypoglossal and the glossopharyngeal nerve of the subject.

* * * * *